US006902905B2

(12) United States Patent
Burson et al.

(10) Patent No.: US 6,902,905 B2
(45) Date of Patent: Jun. 7, 2005

(54) GLUCOSE MEASURING ASSEMBLY WITH A HYDROGEL

(75) Inventors: Kim K. Burson, Redwood City, CA (US); Michelle Van Wyhe, Menlo Park, CA (US); Jeffrey Pudlo, Emerald Hills, CA (US); Michael Reidy, Half Moon Bay, CA (US); Pravin Soni, Sunnyvale, CA (US); Christopher Uhegbu, San Leandro, CA (US); Prema Vijayakumar, Fremont, CA (US)

(73) Assignee: Cygnus, Inc., Redwood City, CA (US)

( * ) Notice: Subject to any disclaimer, the term of this patent is extended or adjusted under 35 U.S.C. 154(b) by 4 days.

(21) Appl. No.: 10/438,239

(22) Filed: May 14, 2003

(65) Prior Publication Data

US 2003/0199745 A1 Oct. 23, 2003

Related U.S. Application Data

(63) Continuation of application No. 09/556,486, filed on Apr. 21, 2000, now Pat. No. 6,615,078.
(60) Provisional application No. 60/130,729, filed on Apr. 22, 1999, now abandoned, and provisional application No. 60/149,513, filed on Aug. 17, 1999, now abandoned.

(51) Int. Cl.[7] .................................................. C12Q 1/54
(52) U.S. Cl. ........................................... 435/14; 422/60
(58) Field of Search ................. 435/14, 25; 205/777.5; 422/60; 424/94.1, 449, 488

(56) References Cited

U.S. PATENT DOCUMENTS

| | | | |
|---|---|---|---|
| 4,020,830 A | 5/1977 | Johnson et al. | |
| 4,200,098 A | * 4/1980 | Ayer et al. | ................... 424/424 |
| 4,406,827 A | 9/1983 | Carim | |
| 4,474,570 A | 10/1984 | Ariura et al. | |
| 4,492,622 A | 1/1985 | Kuypers | |
| 4,684,558 A | 8/1987 | Keusch et al. | |
| 4,702,732 A | 10/1987 | Powers et al. | |
| 4,706,680 A | 11/1987 | Keusch et al. | |
| 4,722,726 A | 2/1988 | Sanderson et al. | |
| 4,722,761 A | 2/1988 | Cartmell et al. | |
| 4,731,049 A | 3/1988 | Parsi | |
| 4,764,164 A | 8/1988 | Sasaki | |
| 4,777,954 A | 10/1988 | Keusch et al. | |
| 4,968,297 A | 11/1990 | Jacobsen et al. | |
| 4,989,607 A | 2/1991 | Keusch et al. | |
| 5,036,861 A | 8/1991 | Sembrowich et al. | |
| 5,037,380 A | 8/1991 | Jacobsen et al. | |
| 5,057,072 A | 10/1991 | Phipps | |
| 5,069,908 A | 12/1991 | Henley | |
| 5,076,273 A | 12/1991 | Schoendorfer et al. | |
| 5,134,057 A | 7/1992 | Kuypers et al. | |
| 5,140,985 A | 8/1992 | Schroeder et al. | |
| 5,143,071 A | 9/1992 | Keusch et al. | |
| 5,152,758 A | 10/1992 | Kaetsu et al. | |
| 5,205,297 A | 4/1993 | Montecalvo et al. | |
| 5,279,543 A | 1/1994 | Glikfeld et al. | |
| 5,291,887 A | 3/1994 | Stanley et al. | |
| 5,330,527 A | 7/1994 | Montecalvo et al. | |
| 5,340,722 A | 8/1994 | Wolfbeis et al. | |
| 5,354,790 A | 10/1994 | Keusch et al. | |
| 5,362,307 A | 11/1994 | Guy et al. | |
| 5,362,308 A | 11/1994 | Chen et al. | |
| 5,405,366 A | 4/1995 | Fox et al. | |
| 5,428,123 A | 6/1995 | Ward et al. | |
| 5,636,632 A | 6/1997 | Bommannan et al. | |
| 5,651,869 A | 7/1997 | Yoshioka et al. | |
| 5,730,714 A | 3/1998 | Guy et al. | |
| 5,735,273 A | 4/1998 | Kurnik et al. | |
| 5,771,890 A | 6/1998 | Tamada | |
| 5,786,216 A | 7/1998 | Dionne et al. | |
| 5,823,957 A | 10/1998 | Faupel et al. | |
| 5,827,183 A | 10/1998 | Kurnik et al. | |
| 5,954,685 A | 9/1999 | Tierney | |
| 5,965,380 A | 10/1999 | Heller et al. | |

(Continued)

FOREIGN PATENT DOCUMENTS

| | | |
|---|---|---|
| EP | 0 304 304 | 2/1989 |
| EP | 0942 278 | 9/1999 |
| WO | WO 91/12772 | 9/1991 |
| WO | WO 92/07619 | 5/1992 |
| WO | WO 92/10234 | 6/1992 |
| WO | WO 93/10163 | 5/1993 |
| WO | WO 95/02357 | 1/1995 |
| WO | WO 96/00109 | 1/1996 |
| WO | WO 96/00110 | 1/1996 |
| WO | WO 97/02811 | * 1/1997 |
| WO | WO 97/10499 | 3/1997 |
| WO | WO 97/24059 | 7/1997 |
| WO | WO 97/38126 | 10/1997 |
| WO | WO 97/42882 | 11/1997 |
| WO | WO 97/42885 | 11/1997 |
| WO | WO 97/42886 | 11/1997 |
| WO | WO 97/42888 | 11/1997 |
| WO | WO 97/43962 | 11/1997 |
| WO | WO 99/58190 | 11/1999 |

OTHER PUBLICATIONS

Abraham W. Hydrogels for Iontophoretic Extractions of Glucose Through Skin. Polymeric Materials Science and Engineering 1997 vol. 76, p. 570.*

(Continued)

*Primary Examiner*—Ralph Gitomer
(74) *Attorney, Agent, or Firm*—Barbara G. McClung; Gary R. Fabian

(57) ABSTRACT

This invention relates to methods for reducing the presence of a compound in an ionically conductive material, e.g., for use in iontophoretic devices, wherein the presence of the compound interferes with detecting a selected analyte. Removal of the compound can typically take place either during or after the manufacture of the ionically conductive material or an assembly comprising this material. Also disclosed are methods for generating selectively permeable barriers on the reactive faces of electrodes. Further, this invention relates to hydrogels comprising one or more biocides, as well as assemblies containing such hydrogels.

19 Claims, 2 Drawing Sheets

U.S. PATENT DOCUMENTS

| | | | | |
|---|---|---|---|---|
| 5,989,409 | A | | 11/1999 | Kurnik et al. |
| 6,018,033 | A | * | 1/2000 | Chen et al. ................... 536/4.1 |
| 6,023,629 | A | | 2/2000 | Tamada |
| 6,083,710 | A | | 7/2000 | Heller et al. |
| 6,121,009 | A | | 9/2000 | Heller et al. |
| 6,139,718 | A | * | 10/2000 | Kurnik et al. ............... 600/347 |
| 6,162,611 | A | | 12/2000 | Heller et al. |
| 6,393,318 | B1 | | 5/2002 | Conn et al. |
| 6,615,078 | B1 | * | 9/2003 | Burson et al. ................. 604/20 |
| 2003/0130427 | A1 | * | 7/2003 | Cleary et al. ............... 525/192 |
| 2003/0170308 | A1 | * | 9/2003 | Cleary et al. ............... 424/486 |
| 2004/0062759 | A1 | * | 4/2004 | Abraham et al. .......... 424/94.1 |

OTHER PUBLICATIONS

Albin et al., "Theoretical and Experimental Studies of Glucose Sensitive Membranes," *Journal of Controlled Release* 6:267–291 (1987).

Allcock et al., "Activity of Urea Amidohydrolase Immobilized Within Poly[di(methoxyethoxyethoxy)phosphazene] Hydrogels," *Biomaterials* 15(7):502–506 (1994).

Asakura et al., "Immobilization of Glucose Oxidase on Nonwoven Fabrics with Bombyx mori Silk Fibroin Gel," *Journal of Applied Chemistry* 46(1):49–53(1992).

D'Urso et al., "Poly(ethylene glycol)–Serum Albumin Hydrogel as Matrix for Enzyme Immbilization: Biomedical Applications," *Art. Cells. Blood Subs., and Immob. Biotech.* 23(5):587–595 (1995).

Glikfeld et al., "Noninvasive Sampling of Biological Fluids by Iontophoresis," *Pharm. Res. (US)* 6(11):988–990 (1989).

Heller et al., "Controlled Drug Release by Polymer Dissolution II: Enzyme–mediated Delivery Device," *J. Pharmaceut. Sci.* 68(7):919–921 (1979).

Kalisz, H.M., et al., "Purification of the Glycoprotein Glucose Oxidase From *Penicillium amagasakiense* by HighPerformace Liquid Chromatography," *Journal of Chromatography* 521:245–250 (1990).

Kost et al., "Glucose Sensitibe Membranes Containing Glucose Oxidase: Activity, Swelling, and Permeability Studies," *J. Biomed. Materials Res.* 19(9):1117–1133(1985).

Meyerhoff et al., "On Line Continuous Monitoring of Subcutaneous Tissue Glucose in Men by Combining Portable Glucosensor with Microdialysis," *Diabetologia (Germany)* 35(11):1087–1092 (1992).

Newman,J.D., et al., "Catalytic Materials, Membranes, and Fabrication Technologies Suitable for the Construction of Amperometric Biosensors," *Analytical Chemistry* 67:4594–4599 (1995).

Tamada et al., "Noninvasive Glucose Monitoring," *JAMA* 282(19):1839–1844 (1999).

Updike et al., "The Enzyme Electrode," *Nature* 214:956–958 (1967).

Wang, Joseph, "Permselective Coatings for Amperometric Biosensing," Chapter 10 in ACS Symposium Series No. 487 *American Chemical Society* (1992).

Welfle, Dr. K., et al., "Glucose Oxidase of *Penicillium notatum*. Purification, Stability and hydrodynamic Properties," *Studia Biophysica* 138(3):245–260 (1990).

\* cited by examiner

GLUCOSE MEASURING ASSEMBLY WITH A HYDROGEL

CROSS-REFERENCE TO RELATED APPLICATION

This application is a continuation of U.S. patent application Ser. No. 09/556,486, filed 21 Apr. 2000, now U.S. Pat. No. 6,615,078, issued 2 Sep. 2003, which claims the benefit of U.S. Provisional Application Nos. 60/130,729, filed 22 Apr. 1999, now abandoned, and 60/149,513, filed 17 Aug. 1999, now abandoned, all of which applications are herein incorporated by reference in their entireties.

TECHNICAL FIELD

This invention relates generally to methods and devices for reducing the presence of a biocide in an ionically conductive material, e.g., for use in iontophoretic devices, either during or after the manufacture of the ionically conductive material or an assembly comprising this material. In addition, this invention relates to hydrogels comprising one or more biocides.

BACKGROUND

A number of diagnostic tests are routinely performed on humans to evaluate the amount or existence of analytes present in blood or other body fluids. These diagnostic tests typically rely on physiological fluid samples removed from a subject, either using a syringe or by pricking the skin.

PCT Publication No. WO 96/00110, published Jan. 4 Jan. 1996, describes an iontophoretic apparatus for transdermal monitoring of a target analyte, wherein an iontophoretic electrode is used to move the analyte into a collection reservoir and a biosensor is used to detect the analyte. In U.S. Pat. No. 5,279,543 to Glikfeld, iontophoresis is used to sample a substance through skin and into a receptacle on the skin surface. Glikfeld suggests that this sampling procedure can be coupled with a glucose-specific biosensor or glucose-specific electrodes in order to monitor blood glucose. Additionally, U.S. Pat. Nos. 5,362,307 and 5,730,714 both to Guy, et al. describe sampling devices.

Analytical biosensors have been embraced during the last decade as a means of combining the advantages of electrochemical signal transduction with the specificity inherent in biological interactions. However, two factors that may affect the quality of the data generated by the signal transduction are as follows. First, compounds unrelated to the analyte of interest may enter the analytical system and interact directly with the electrode assembly, leading to signal generation unrelated to the concentration of the analyte or its derivatives. These interfering species may be introduced either during manufacture of the biosensor or during its use. For example, certain compounds present in sample fluid (e.g., acetominophen and uric acid) are electrochemically "active" and are capable of signal generation independent of the specific biological system employed by the biosensor, via a direct interaction with the electrode. Additionally, compounds that may interact at an electrode may have been introduced during manufacturing for specific purposes, such as to provide antimicrobial or antifungal activity (biocides). These interfering species may produce overlapping current signals, thus decreasing the selectivity of the biosensor. Additionally, the compounds may irreversibly bind to the reactive face of the electrode assembly, leading to fouling of the sensing surface and reduced sensitivity.

Several techniques have been employed to minimize the effects of interfering species on electrode function to get around these issues. One technique is to use the lowest polarizing voltage sufficient for the intended reaction. This reduces the current (i.e., electrons) generated by any undesired electrochemical oxidations requiring polarizing voltages higher than what is required for the intended reaction. However, because some enzymatic systems employed in biosensors require voltage levels that do not provide sufficient screening of signals generated by interfering species, the voltage level cannot be decreased below that which allows generation of signals from the interfering species.

A second technique has been to construct membranes or other physical barriers to impede the interfering species from reaching the face of the electrode. The list of films which may be employed includes cellulose acetate, poly(o-phenylenediamine), polyphenol, polypyrrole, polycarbonate, and Nafion® (E.I du Pont de Nemours & Co., Wilmington Del.) polymer. However, such membranes can be difficult to prepare and may not efficiently attach to the reactive surface of the electrode. There remains a need in the art for methods and devices which provide an efficient reduction of interfering species while maintaining efficient detection of an analyte.

SUMMARY OF THE INVENTION

The present invention provides methods and devices for reducing the presence of a compound in an ionically conductive material wherein the presence of the compound interferes with detecting an analyte in the material. By decreasing the level of interfering species present in the ionically conductive material, the present invention increases the percentage of signal that arises from an analyte of interest (or its derivatives) during use of a sampling device. In one aspect of the present invention, the reduction in interferant signal is achieved by selectively adsorbing the interfering compound from the ionically conductive material before the compound can reach the sensor means and generate a signal. In a second aspect of the invention, the interfering species are reduced by polymerizing an interfering compound to form an electrochemically-inactive but permeation selective barrier at the reactive face of the sensor means. The permeation selective characteristics of the polymer barrier can provide the added benefit of reducing signals generated from interferants other than the species being polymerized. Because the aforementioned permeation selective barrier is created on the reactive face of the sensor means in rather than prior to construction of the collection assembly, the present invention provides efficient means for manufacturing collection assemblies that use this method for reducing the presence of an interferant compound.

Accordingly, it is a general object of the invention to provide a method for reducing the presence of a compound in an ionically conductive material wherein the presence of the compound interferes with detecting an analyte in the material. In one embodiment, the method includes placing the material containing the compound in contact with at least one component of a device used for detecting the analyte, wherein the component is partially permeable to the compound. The component and the compound are contacted under conditions that allow the compound to migrate out of the material and into the component, thus reducing the presence of the compound in the material. In the present invention, the component is preferably composed of a polyurethane-like material or a polyester-like material.

In another embodiment of the present invention, the presence of an interfering compound is reduced essentially as follows. The ionically conductive material containing the interfering compound is placed in contact with a reactive face of a sensor element (for example, a sensor electrode). The ionically conductive material and the sensing element are arranged such that when a current is flowing to the sensing element, the current flows through the ionically conductive material containing the compound. The sensor element is then activated to provide an electrical current for a period of time and under conditions sufficient to polymerize the compound on the reactive face of the sensor. Previous approaches for forming permeably selective films on electrodes required that the film was formed ex situ, that is before use, and the present invention demonstrates that the permeably selective barrier can be formed in situ. In the present invention, a preferred group of polymerizable interferant compounds are phenolic compounds, for example the p-hydroxybenzoic acid esters commonly referred to as "parabens."

In a further embodiment of the invention, a method of forming a permeation-selective barrier on an electrode face in situ is described, the method comprising the steps of a) formulating an ionically conductive material comprising a phenolic compound capable of polymerizing under the influence of an electrical current, b) placing the material in contact with a reactive face of a sensing electrode such that when current is flowing to the electrode current flows through the material, and c) activating the electrode to provide an electrical current for a period of time and under conditions sufficient to polymerize the compound on the reactive face of the sensor and form a permeation-selective barrier. In the present invention, a preferred group of phenolic compounds are the p-hydroxybenzoic acid esters commonly referred to as "parabens."

In another embodiment of the present invention, a collection assembly for use in a sampling system is described. The collection assembly is comprised of a collection insert layer containing an ionically conductive material, wherein the ionically conductive material contains a compound that will polymerize on the reactive face of a sensor element placed adjacent to the ionically conductive material. Also described is a method of manufacturing a collection assembly The method of manufacture of the collection assembly comprises the steps of a) forming the ionically conductive medium containing the interfering compound, b) contacting one surface of the ionically conductive medium with a mask layer composed of a material that is substantially impermeable to the selected analyte or derivatives thereof, and c) contacting a second surface of the ionically conductive medium with a retaining layer to form the collection assembly.

In a further embodiment of the present invention, an autosensor assembly for use in a sampling system is described. The autosensor assembly is comprised of a) a collection insert layer containing an ionically conductive medium, an enzyme capable of reacting with an analyte to produce hydrogen peroxide, and a phenolic compound which will polymerize under an electric current; and b) a sensor element in operative contact with the collection insert layer, positioned such that the phenolic compound can react electrochemically with the reactive face of the sensor element to provide a selectively permeable barrier at an interface between the sensor element and the collection insert layer.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

1. Definitions

Figure 1:
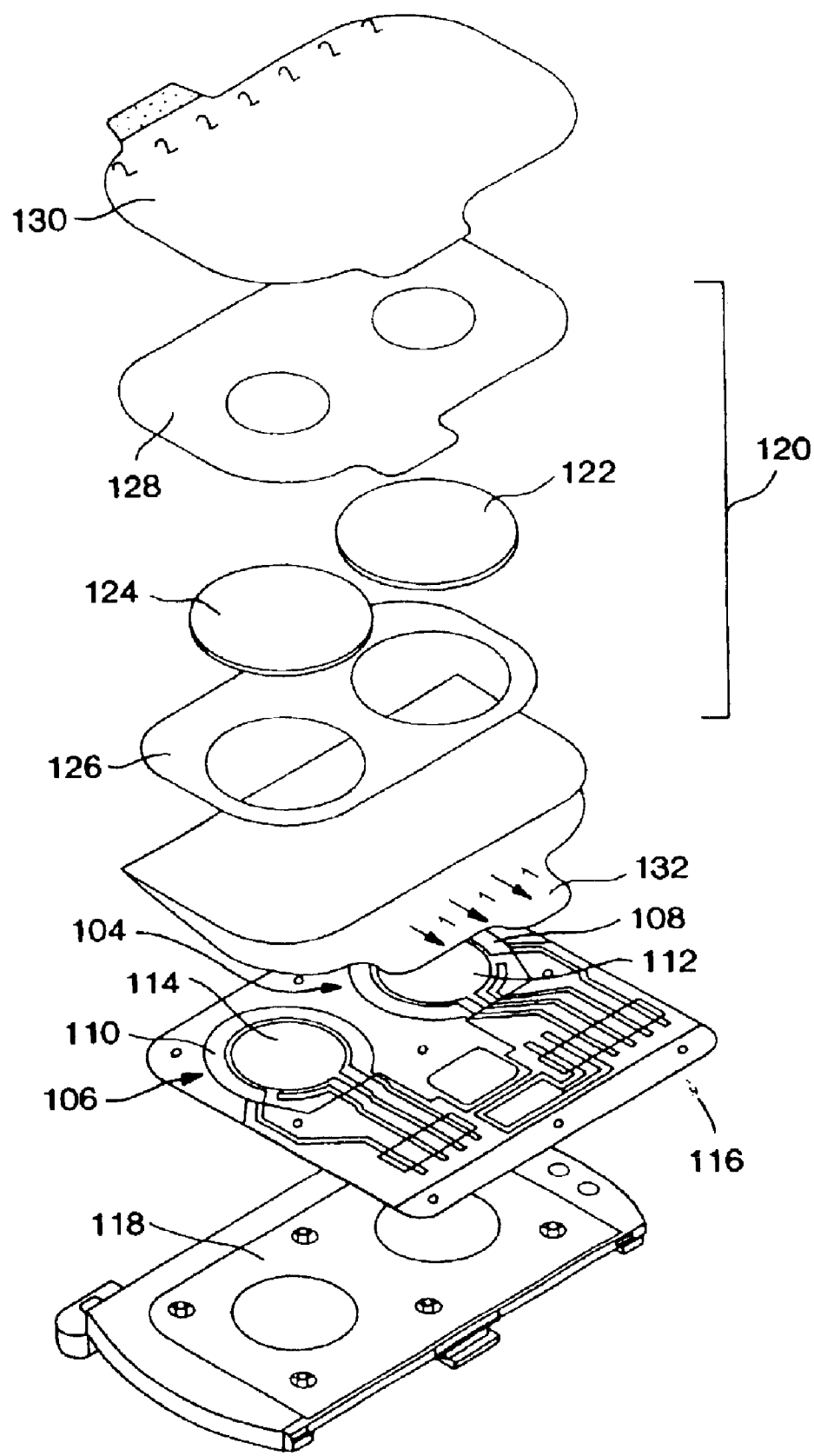
FIG. 1 is an exploded pictorial representation of components from an exemplary sampling system.

Before describing the present invention in detail, it is to be understood that this invention is not limited to particular compositions or biological systems as such may, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a reservoir" includes a combination of two or more such reservoirs, reference to "an analyte" includes mixtures of analytes, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

The terms "analyte" and "target analyte" are used herein to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

The term "interferant" or "interfering species" refers to an electroactive compound other than the analyte of interest which, when present in an ionically conductive material, generates a response unrelated to the concentration (or amount) of analyte being measured by the sampling system, thus interfering with the detection of an analyte in the material.

The term "biocide" is used herein to describe any substance that kills or inhibits the growth of micro-organisms, including but not limited to, viruses, bacteria, molds, slimes, yeast and fungi. A biocide may be a material that is also toxic to humans, but is preferably a material which, when used in relatively low concentrations, in an ionically conductive material such as a patch or a hydrogel, does not cause skin irritation or any adverse effects on the human subject.

A "sampling device," "sampling mechanism" or "sampling system" refers to any device for obtaining a sample from a biological system for the purpose of determining the concentration of an analyte of interest. Such "biological systems" include any biological system from which the analyte of interest can be extracted, including, but not limited to, blood, interstitial fluid, perspiration and tears. Further, a "biological system" includes both living and artificially maintained systems. As used herein, the term "sampling" mechanism refers to extraction of a substance from the biological system, generally across a membrane such as the stratum corneum or mucosal membranes, by invasive, minimally invasive, or non-invasive means. The membrane can be natural or artificial, and can be of plant or animal nature, such as natural or artificial skin, blood vessel tissue, intestinal tissue, and the like. Typically, the sampling mechanism are in operative contact with a "reservoir," or "collection reservoir," wherein the sampling mechanism is used for extracting the analyte from the biological system into the reservoir to obtain the analyte in the reservoir. Non-limiting examples of sampling techniques include iontophoresis, sonophoresis (see, e.g., International Publication No. WO 91/12772, published Sep. 5, 1991), suction, electroporation, thermal poration, passive diffusion (see, e.g., International Publication Nos.: WO 97/38126 (published Oct. 16 Oct. 1997); WO 97/42888, WO 97/42886, WO 97/42885, and WO 97/42882 (all published Nov. 20 Nov. 1997); and WO 97/43962 (published 27 Nov. 1997), microfine (miniature) lances or cannulas, subcutaneous implants or insertions, and laser devices (see, e.g., Jacques et al. (1978) *J. Invest. Dermatology* 88:88–93; International Publication WO 99/44507, published 10 Sep. 1999; International Publication WO 99/44638, published 10 Sep. 1999; and International Publication WO 99/40848, published 19 Aug. 1999). Iontophoretic sampling devices are described, for example, in International Publication No. WO 97/24059, published 10 Jul. 1997; European Patent Application EP 0942 278, published 15 Sep. 1999; International Publication No. WO 96/00110, published 4 Jan. 1996; International Publication No. WO 97/10499, published 2 Mar. 1997; U.S. Pat. Nos. 5,279,543; 5,362,307; 5,730,714; 5,771,890; 5,989,409; 5,735,273; 5,827,183; 5,954,685 and 6,023,629, all of which are herein incorporated by reference in their entireties.

The term "physiological fluid" as used herein refers to any desired fluid to be sampled, and includes, but is not limited to, blood, cerebrospinal fluid, interstitial fluid, semen, sweat, saliva, urine and the like.

The term "artificial," as used herein, refers to an aggregation of cells of monolayer thickness or greater which are grown or cultured in vivo or in vitro, and which function as a tissue of an organism but are not actually derived, or excised, from a pre-existing source or host.

A "monitoring system," as used herein, refers to a system useful for frequently measuring a physiological analyte present in a biological system. Such a system typically includes, but is not limited to, sampling mechanism, sensing mechanism, and a microprocessor mechanism in operative communication with the sampling mechanism and the sensing mechanism.

As used herein, the term "frequent measurement" intends a series of two or more measurements obtained from a particular biological system, which measurements are obtained using a single device maintained in operative contact with the biological system over a time period in which a series of measurements (e.g, second, minute or hour intervals) is obtained. The term thus includes continual and continuous measurements.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female.

The term "transdermal," as used herein, includes both transdermal and transmucosal techniques, i.e., extraction of a target analyte across skin, e.g., stratum corneum, or mucosal tissue. Aspects of the invention which are described herein in the context of "transdermal," unless otherwise specified, are meant to apply to both transdermal and transmucosal techniques.

The term "transdermal extraction," or "transdermally extracted" intends any sampling method, which entails extracting and/or transporting an analyte from beneath a tissue surface across skin or mucosal tissue. The term thus includes extraction of an analyte using, for example, iontophoresis (reverse iontophoresis), electroosmosis, sonophoresis (see, e.g., U.S. Pat. No. 5,636,632), microdialysis, suction, and passive diffusion. These methods can, of course, be coupled with application of skin penetration enhancers or skin permeability enhancing technique such as various substances or physical methods such as tape stripping or pricking with micro-needles. The term "transdermally extracted" also encompasses extraction techniques which employ thermal poration, laser microporation, electroporation, microfine lances, microfine canulas, subcutaneous implants or insertions, and the like.

The term "iontophoresis" intends a method for transporting substances across tissue by way of an application of electrical energy to the tissue. In conventional iontophoresis, a reservoir is provided at the tissue surface to serve as a container of (or containment means for) material to be transported. Iontophoresis can be carried out using standard methods known to those of skill in the art, for example by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode). For example, see U.S. Pat. Nos. 5,771,890 and 6,023,629 and PCT Publication No. WO 96/00109, published 4 Jan. 1996.

The term "reverse iontophoresis" refers to the movement of a substance from a biological fluid across a membrane by way of an applied electric potential or current. In reverse iontophoresis, a reservoir is provided at the tissue surface to receive the extracted material, as used in the GlucoWatch® (Cygnus, Inc., Redwood City, Calif.) glucose monitor (See, e.g., Tamada et al. (1999) *JAMA* 282:1839–1844).

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," "sensing mechanism," or "biosensor device" encompasses any device that can be used to measure the concentration or amount of an analyte, or derivative thereof, of interest. Preferred sensing devices for detecting blood analytes generally include electrochemical devices, optical and chemical devices and combinations thereof. Examples of electrochemical devices include the Clark electrode system (see, e.g., Updike, et al., (1967) *Nature* 214:986–988), and other amperometric, coulometric, or potentiometric electrochemical devices. Examples of optical devices include conventional enzyme-based reactions as used in the Lifescan® (Johnson and Johnson, New Brunswick, N.J.) glucose monitor (see, e.g., U.S. Pat. No. 4,935,346 to Phillips, et al.).

A "biosensor" or "biosensor device" includes, but is not limited to, a "sensor element" which includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors are described by Newman, J. D., et al.(1995) *Analytical Chemistry* 67:4594–4599.

The "sensor element" can include components in addition to the sensing electrode, for example, it can include a "reference electrode" and a "counter electrode." The term "reference electrode" is used herein to mean an electrode that provides a reference potential, e.g., a potential can be established between a reference electrode and a working electrode. The term "counter electrode" is used herein to mean an electrode in an electrochemical circuit that acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are preferred.

In one embodiment, the "counter electrode" of the "sensor element" comprises a "bimodal electrode." The term "bimodal electrode" as used herein typically refers to an electrode which is capable of functioning non-simultaneously as, for example, both the counter electrode (of the "sensor element") and the iontophoretic electrode (of the "sampling mechanism") as described, for example, U.S. Pat. No. 5,954,685.

The terms "reactive surface," and "reactive face" are used interchangeably herein to mean the surface of the sensing electrode that: (1) is in contact with the surface of an ionically conductive material which contains an analyte or through which an analyte, or a derivative thereof, flows from a source thereof, (2) is comprised of a catalytic material (e.g., carbon, platinum, palladium, rhodium, ruthenium, or nickel and/or oxides, dioxides and combinations or alloys thereof) or a material that provides sites for electrochemical reaction; (3) converts a chemical signal (for example, hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

An "ionically conductive material" refers to any material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a hydrogel, a sponge or pad (e.g., soaked with an electrolytic solution), or any other material that can contain an electrolyte and allow passage of electrochemically active species, especially the analyte of interest.

The term "buffer" refers to one or more components which are added to a composition in order to adjust or maintain the pH of the composition.

The term "electrolyte" is used herein to a component of the ionically conductive medium which allows for an ionic current to flow within the medium. This component of the ionically conductive medium can be one or more salts or buffer components, but is not limited to these materials.

The term "humectant" is used herein to describe a substance which has an affinity for water or a stabilizing effect on the water content of a composition.

The term "collection reservoir" is used to describe any suitable containment means for containing a sample extracted from a biological system. For example, the collection reservoir can be a receptacle containing a material which is ionically conductive (e.g., water with ions therein), or alternatively it can be a material, such as a sponge-like material or hydrophilic polymer, used to keep the water in place. Such collection reservoirs can be in the form of a hydrogel (for example, in the shape of a disk or pad). Hydrogels are typically referred to as "collection inserts." Other suitable collection reservoirs include, but are not limited to, tubes, vials, strips, capillary collection devices, cannulas, and miniaturized etched, ablated or molded flow paths.

A "collection insert layer" is a layer of an assembly or laminate comprising a collection reservoir (or collection insert) located, for example, between a mask layer and a retaining layer.

The term "permeation selective" or "permselective" refers to a property of a membrane barrier wherein passage through the membrane is selective, depending upon the physical and chemical properties of the membrane as well as those of the compound involved. For example, permselective films allow the transport of an analyte or its derivatives, while preventing undesirable compounds (interferants) from passing. (See, for instance, Chapter 10, "Permselective Coatings for Amperometric Biosensing" in ACS Symposium Series No. 487 (1992) American Chemical Society.) A "laminate", as used herein, refers to structures comprised of at least two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, pressure sensitive adhesives, thermoset adhesives, cyanocrylate adhesives, epoxies, contact adhesives, and heat sensitive adhesives.

A "collection assembly", as used herein, refers to structures comprised of several layers, where the assembly includes at least one collection insert layer, for example a hydrogel. An example of a collection assembly as referred to in the present invention is a mask layer, collection insert layer, and a retaining layer where the layers are held in appropriate functional relationship to each other but are not necessarily a laminate (i.e., the layers may not be bonded together. The layers may, for example, be held together by interlocking geometry or friction).

The term "mask layer" as used herein refers to a component of a collection assembly that is substantially planar and typically contacts both the biological system and the collection insert layer. See, for example, U.S. Pat. Nos. 5,735,273, and 5,827,183, herein incorporated by reference.

The term "gel retaining layer" or "gel retainer" as used herein refers to a component of a collection assembly that is substantially planar and typically contacts both the collection insert layer and the electrode assembly.

The term "support tray" as used herein typically refers to a rigid, substantially planar platform and is used to support and/or align the electrode assembly and the collection assembly. The support tray provides a means for placing the electrode assembly and the collection assembly into the sampling system.

An "autosensor assembly", as used herein, refers to a structure generally comprising a mask layer, collection insert layer, a gel retaining layer, an electrode assembly, and a support tray. The autosensor assembly may also include liners where the layers are held in approximate, functional relationship to each other. Exemplary collection assemblies and autosensor structures are described, for example, in International Publication WO 99/58190, published 18 Nov. 1999; and U.S. Pat. Nos. 5,735,273 and 5,827,183. The mask and retaining layers are preferably composed of materials that are substantially impermeable to the analyte (chemical signal) to be detected; however, the material can be permeable to other substances. By "substantially impermeable" is meant that the material reduces or eliminates chemical signal transport (e.g., by diffusion). The material can allow for a low level of chemical signal transport, with the proviso that chemical signal passing through the material does not cause significant edge effects at the sensing electrode.

The term "in situ" refers to the location of an occurrence with respect to an original position. In the case of the present invention, the term refers to the formation of a permselective polymer barrier on the reactive face of a sensing element, this being the original position or place of contact between the sensing element and the ionically conductive material comprising the compound to be polymerized.

The terms "about" or "approximately" when associated with a numeric value refers to that numeric value plus or minus 10 units of measure (i.e. percent, grams, degrees or volts), preferably plus or minus 5 units of measure, more preferably plus or minus 2 units of measure, most preferably plus or minus 1 unit of measure.

By the term "printed" as used herein is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, or the like.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

2. General Methods Biocides, and Formulations

Methods and devices for reducing the presence of a compound in an ionically conductive material wherein the presence of the compound interferes with detecting an analyte in the material are provided by this invention. Further included in the present invention is an apparatus incorporating the methods and devices described herein. The methods and apparatus may be employed in a sampling system, to enhance the detection and/or quantification of the concentration of a target analyte present in a biological system. Although the methods and apparatus are broadly applicable to sampling any chemical analyte and/or substance, the preferred embodiment of the invention is used in transdermal sampling and quantifying or qualifying glucose or a glucose metabolite.

As will be understood by the ordinarily skilled artisan upon reading the specification, the analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse (e.g., ethanol, cocaine), therapeutic and/or pharmacologic agents, electrolytes, physiological analytes of interest (e.g., calcium, potassium, sodium, chloride, bicarbonate ($CO_2$), glucose, urea (blood urea nitrogen), lactate or lactic acid, hematocrit, and hemoglobin), lipids, and the like. In preferred embodiments, the analyte is a physiological analyte of interest, for example glucose, or a chemical that has a physiological action, for example a drug or pharmacological agent.

During manufacture of the autosensor assembly, one or more biocides may be incorporated into the ionically conductive material. Biocides of interest for the methods of the present invention include, but are not limited to, compounds such as chlorinated hydrocarbons; organometallics; hydrogen releasing compounds; metallic salts; organic sulfur compounds; phenolic compounds (including but not limited to a variety of Nipa Hardwicke Inc. liquid preservatives registered under the trade names Nipastat®, Nipaguard®, Phenosept®, Phenonip®, Phenoxetol®, and Nipacide®); quartenary ammonium compounds; surfactants and other membrane-disrupting agents (including but not limited to undecylenic acid and its salts), and the like. However, the biocides often act as interfering species. The present disclosure teaches formulations incorporating biocides into components of an autosensor assembly as well as methods of removing such biocides after manufacture of the autosensor assembly and assembly components.

One biocide used in the practice of the present invention is undecylenic acid (10-undecenoic acid, or UA). Undecylenic acid is an unsaturated fatty acid which has been used since the 1940's as an relatively nonirritating and reasonably effective treatment for preventing the growth of pathogenic organisms on the skin. Both the acid form ("undecylenic acid") and the salt forms ("undecylenates") have biocidic activity, and may be used in combination with one another (or with other biocides). The biocide is commonly referred to herein as "undecylenic acid" without differentiation between the acid and salt forms. The salt forms may include but are not limited to the sodium, calcium and zinc salts. In addition, other esters of undecylenate, including but not limited to the methyl, ethyl, propyl, isopropyl, glyceryl, benzyl, allyl and epoxypropyl esters, are effective as biocides. When used as a biocide in the hydrogels of the present invention, the undecylenate biocide (acid, salt or mixture thereof) is present in the hydrogel at a concentration high enough to be effective as a biocide, for example between about 0.001 wt % and about 10 wt %, preferably between about 0.01 wt % and about 5 wt %, more preferably between about 0.1 wt % and about 2 wt %.

Another preferred biocide is Nipastat® sodium p-hydrozybenzoic acid esters (Nipa Hardwicke, Inc., Wilmington Del.). Nipastat® biocide is a mixture of sodium derivatives of p-hydroxybenzoate. The major component of the mixture is methyl paraben (methyl p-hydroxybenzoate) with minor components of the ethyl-, propyl-, butyl-, and iso-butyl-p-hydroxybenzoates. Any such parabens can be used in the practice of the present invention, individually or preferably in mixtures. In addition, mixtures of different types of biocides can be used (e.g., parabens plus other biocides). When used as a biocide in the hydrogels of the present invention, the Nipastat® biocide is present in the hydrogel at a concentration high enough to be effective as a biocide, for example between about 0.001 wt % and about 10 wt %, preferably between about 0.01 wt % and about 5 wt %, more preferably between about 0.1 wt % and about 2 wt %.

Experiments performed in support of the present invention show that these biocides, when incorporated into a collection reservoir or collection reservoir material (e.g., a hydrogel), are effective biocides against a number of microbial organisms, including, but not limited to, *Aspergillus niger, Candida albicans, Eschericia coli, Pseudomonas aeruginosa* and *Staphylococcus aureus.*

The collection reservoir typically contains an ionically conductive liquid or liquid-containing medium. In one embodiment, the collection reservoir is preferably a hydrogel which can contain ionic substances, or electrolytes, in an amount sufficient to produce high ionic conductivity. The hydrogel is formed from a solid material (solute) which, when combined with water, forms a gel by the formation of a structure which holds water including interconnected cells and/or network structure formed by the solute. Suitable hydrogel formulations are described in PCT Publication Nos. WO 97/02811, published 30 Jan. 1997, and WO 96/00110, published 4 Jan. 1996. The solute may be a naturally occurring material such as the solute of natural gelatin which includes a mixture of proteins obtained by the hydrolysis of collagen by boiling skin, ligaments, tendons and the like. However, the solute or gel forming material is more preferably a polymer material (including, but not limited to, polyethylene oxide, polyvinyl alcohol, polyacrylic acid, polyacrylamidomethylpropanesulfonate and mixtures and/or copolymers thereof) present in an amount in the range of more than 0.5% and less than 40% by weight, preferably 8 to 12% by weight when a humectant is also added, and preferably about 15 to 20% by weight when no humectant is added.

While not required, crosslinking of the polymer may be performed to improve the structural integrity of the hydrogel. The crosslinking may be achieved by thermal reaction, chemical reaction or by providing ionizing radiation (for example, electron beam radiation, UV radiation or gamma radiation). Various agents which can be used to facilitate crosslinking within a polymer in conjunction with ionizing radiation are disclosed in U.S. Pat. Nos. 4,684,558 and 4,989,607 incorporated herein by reference. Crosslinkers which may be used in the present invention include but are not limited to N,N-methylenebisacrylamide, polypropylene glycol monomethacrylate, polypropylene glycol monoacrylate, polyethylene glycol dimethacrylate, polyethylene glycol diacrylate, triallylisocyanurate (TAIC), diallylisocyanurate (DAIC), triacrylates such as SR 454 ethoxylated trimethylolpropane triacrylate, and SR 9035 highly alkoxylated trimethylolpropane triacrylate, available from Sartomer (Exton, Pa.), ethylene glycol methacrylate, triethylene glycol methacrylate, trimethylolpropane trimethacrylates, and glutaraldehyde. Furthermore, a photoinitiator may be used to facilitate the crosslinking process.

In addition to crosslinking of the polymer, the ionically conductive medium of the present invention may comprise a structural support which is embedded in the hydrogel. This support includes, but is not limited to, a woven fabric, a nonwoven fabric, dispersed fibers, or a membrane. The ionically conductive medium can be polymerized separately, or in the presence of this "scrim" or nonwoven material such as polyester or polypropylene. Two exemplary nonwoven materials are Delnet® nonwoven and Remay® nonwoven, available from AET Specialty Nets.

Additional materials may be added to the hydrogel, including, without limitation, one or more electrolytes (e.g., salts), buffers, tackifiers, humectants, crosslinkers, biocides, preservatives, chelators (for example, ethylenediamine tetraacetic acid) and enzyme stabilizers. A variety of buffers may be used in connection with the present invention, including but not limited to various salts of phosphate, citrates, bicarbonates, succinates, acetates and lactates. One preferred buffer is phosphate buffer. The buffer is preferably present in amounts to maintain the pH of the hydrogel in a range of about pH 3–9, more preferably pH 6–8. A preferred electrolyte is sodium chloride, but other salts may be equally employed. Humectants useful in the present invention include, but are not limited to, glycerol, hexylene glycol and sorbitol.

In one aspect, the present invention relates to hydrogels containing a biocide of interest. For example, a hydrogel, comprises, (a) a hydrophilic compound which forms a gel in the presence of water, which compound is present in an amount of about 4% or more by weight based on the total weight of the hydrogel;

(b) water in an amount of about 95% or less based on the total weight of the hydrogel;

(c) an electrolyte, wherein background electrical signal in the gel is less than approximately 200 nA;

(d) an enzyme composition; and (e) a biocide.

Exemplary biocides include, but are not limited to chlorinated hydrocarbons, organometallics, hydrogen releasing compounds, metallic salts, quaternary ammonium compounds, organic sulfur compounds, phenolics, and methylparabens. Preferred biocides of the present invention include undecylenates (e.g., undecylenic acid, a salt of undecylenic acid, or mixtures thereof), and parabens. Biocides may be, for example, antimicrobial and/or antifungal.

Typically, the background electrical signal in a gel is in the range of about 20 to about 250 nA, preferably between about 25 to about 100 nA, more preferably between about 30 and about 90 nA, for example, about 50 nA.

Exemplary enzyme compositions are discussed herein. Use of a selected enzyme depends on the analyte which is to be detected. In one embodiment, for the detection of glucose, such an enzyme is glucose oxidase. The glucose oxidase may be present in an amount of from about 10 units to about 5,000 units per gram of the total weight of the hydrogel, preferably approximately 200 units or more. Degradative components of the enzyme composition are reduced such that quantitation of the analyte is not compromised, for example, the glucose oxidase can catalyze a reaction between glucose and oxygen resulting in the generation of hydrogen peroxide; accordingly, the hydrogen peroxide degradative components of the enzyme composition are reduced such that quantitation of hydrogen peroxide produced by the glucose oxidase reaction is not compromised. An enzyme composition may also include multiple enzymes used for the detection of one (e.g., analyte glucose, enzyme composition glucose oxidase and mutarotase) or more analytes. Enzyme compositions for use in the practice of the present invention may be from recombinant and/or synthetic sources. Typically, the enzyme is present in an amount of from about 10 units to about 5,000 units per gram of the total weight of the hydrogel.

An exemplary electrolyte is a salt, for example, a chloride salt, preferably, NaCl. Background signal in the hydrogels of the present invention can be determined by a number of standard methods. In the present invention, the background electrical signal is typically less than approximately 200 nA, preferably less than about 100 nA, more preferably less than about 50 nA. Components of the hydrogel, may be treated to remove compounds that cause background electrical signal, for example, using a diafiltration procedure to remove electroactive compounds therefrom.

Hydrogel compositions of the present invention may include manufactured sheets of hydrogel material as well as individual, essentially circular hydrogels.

In addition to the above components, the hydrogels may further comprise a buffering agent present in an amount sufficient to maintain a pH in the hydrogel in a range of from about 3 to about 9, preferably in a range of about pH 6 to about pH 8, and more preferably the buffering agent is sufficient to maintain a pH of about 7.4. An exemplary buffer is a phosphate buffer.

Hydrophilic compounds used to generate hydrogels are discussed herein and include, but are not limited to, polyethylene oxide, polyacrylic acid, polyvinyl alcohol, polyacrylamidomethylpropane-sulfonate, copolymers thereof, and combinations thereof. As discussed herein, the hydrophilic compound may further comprise cross-linking agent(s), e.g., bisacrylamide. The formulations of the present invention may be made with or without a humectant. The hydrophilic compound may be present in an amount of less than about 40% by weight and water is present in an amount of more than 60% by weight based on the weight of the hydrogel, preferably, the hydrophilic compound which forms a gel is present in an amount in the range of from about 1% to about 25%, preferably in the range of about 5% to about 20%, more preferably about 10% to about 15%, based on total weight of the hydrogel. Alternatively, when a humectant is used, the hydrophilic compound is preferably in the range of from about 8% to about 12% based on total weight of the hydrogel containing the humectant.

Further, the hydrogel may comprise a structural support material embedded in the hydrogel. Examples of such support materials are given herein. The support material may, for example, be a nonwoven material. Also as discussed herein, the hydrogel is typically substantially planar and has first and second surfaces, on which a mask layer, and/or gel retaining layer, and/or further release liners (e.g., see FIG. 1) may be disposed. The hydrogel also has sufficient flexibility so as to conform to human skin.

The hydrogels are substantially planar and have a thickness in a range of about 1 mil to about 60 mils, preferably about 1 mil to about 25 mils, more preferably about 5 mils to about 10 mils. In a preferred embodiment, the hydrogel has first and second surface areas, and each surface area is in a range of about 0.5 $cm^2$ to about 10 $cm^2$, more preferably between about 0.5 $cm^2$ to about 2.5 $cm^2$, and the hydrogel has a thickness of from about 1 mil to 10 mils. In a preferred embodiment, a hydrogel disk is about ¾ inch in diameter±15% (i.e., 0.44 sq. in.±0.07 sq. in.) and has a thickness of about 5 mils.

In another aspect, the present invention relates to the discovery that a compound, e.g., a biocide, may be formulated into an ionically conductive material, even though the compound may interfere with detecting an analyte in the ionically conductive material, because the presence of the compound may be reduced by placing the ionically conductive material, comprising the compound, in contact with at least one component comprised of a material that is partially permeable to the compound, under conditions that allow the compound to migrate out of the ionically conductive material and into the component—thus reducing the presence of the compound in the ionically conductive material. In this embodiment the ionically conductive material (ICM) comprising the compound is placed in contact with the component or material (into which it can migrate) under conditions and for a sufficient period of time prior to use of the ionically conductive material in order to reduce the concentration of the compound before use of the ICM. Following the guidance of the specification, in particular the Examples, such conditions and times can be determined for any compound of interest (e.g., biocides). The ability of a selected compound to migrate into a selected material or component can be evaluated as described, for example, in Examples 1, 2, and 3.

This discovery is useful, for example, in that biocide(s) (such as, undecylenates or parabens) can be used in the manufacturing stages of a hydrogel but can be removed from the hydrogel before its use in detecting the presence of a selected analyte. For example, where the collection inserts are hydrogels (FIG. 1, 122, 124), the essentially circular hydrogel disks may be made from a water solution of polyethylene oxide, phosphate buffer, and glucose oxidase, impregnated in a 0.004 inch thick nonwoven PET (e.g., Remay™ #2250 or Delnet™). This composite begins as roll stock from which circular discs are cut. These circular disks ("hydrogels") are then placed into contact with the mask and gel retaining layer materials as shown in FIG. 1 and subsequently used in collecting samples of analyte. During the manufacturing of the hydrogel disks concentrations of the biocide(s) effective to greatly reduce or prevent growth of microorganisms can be used. Then, upon assembly of, for example, an autosensor where the hydrogels are now in contact with materials into which the biocides can migrate, the biocides can migrate into such materials thus reducing the concentration of the biocide in the hydrogel before use of the autosensor to detect analyte concentration (by, for example, placing the autosensor into a monitoring system).

Accordingly, in one aspect of the present invention a method is described for reducing a presence of a compound (e.g., a biocide) in an ionically conductive material wherein, for example, the presence of the compound interferes with detecting an analyte in the material. In one embodiment, the method comprises placing the ionically conductive material (comprising the compound) in contact with at least one material (e.g., a component of a device capable of detecting the analyte) wherein the material/component is at least partially permeable to the compound. Contact is maintained under conditions that allow the compound to migrate out of the ionically conductive material and into the material/component, thus reducing the presence of the compound in the ionically conductive material.

Exemplary biocides for use in the present invention include, but are not limited to, undecylenic acid and phenolic compounds (e.g., parabens, such as an ester of p-hydroxybenzoic acid or mixtures thereof, such esters may include methyl ester, ethyl ester,propyl ester, butyl ester, and isobutyl ester).

Exemplary materials into which such compounds may migrate include, but are not limited to, polyester(s), polyurethane(s), polyethylene(s), acrylic co-polymers, styrene butadiene copolymers, and mixtures thereof.

In one embodiment, the analyte of interest is glucose and the ionically conductive medium comprises part of a collection assembly capable of being used in an iontophoretic sampling device, for example, the collection assembly shown in FIG. 1. In this embodiment, the collection assembly comprises, (i) a collection insert layer comprising the ionically conductive material containing the compound, wherein the ionically conductive material has a first surface and a second surface, (ii) a mask layer comprising a material that is substantially impermeable to the selected analyte or derivatives thereof, wherein the mask layer (a) has an inner face and an outer face and the inner face is positioned in facing relationship with the first surface of the collection insert, and (b) defines an opening that exposes at least a portion of the first surface of the collection insert layer, and (iii) a retaining layer having an inner face and an outer face wherein the inner face is positioned in facing relationship with the second surface of the collection insert, and wherein the retaining layer defines an opening that exposes at least a portion of the second surface of the collection insert layer. Such a mask layer and/or retaining layer can be comprised of, for example, a polyurethane-like material or a polyester-like material, i.e., a material into which the compound can migrate. Exemplary materials into which such compounds may migrate include, but are not limited to, polyester(s), polyurethane(s), polyethylene(s), acrylic co-polymers, styrene butadiene copolymers, and mixtures thereof. Other liners (e.g., FIG. 1, 130, 132) used in such assemblies may be made of materials permeable to the compound or of materials impermeable to the compound.

The present invention also includes methods of manufacturing hydrogels and collections assemblies of the present invention. For example, producing hydrogels containing biocides and placing the hydrogels in contact with a material into which the biocides can migrate.

3. Exemplary Analytes

The analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse (e.g., ethanol, cocaine), therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate and/or lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. In preferred embodiments, the analyte is a physiological analyte of interest, for example glucose, or a chemical that has a physiological action, for example a drug or pharmacological agent.

In order to facilitate detection of the analyte, an enzyme can be disposed within the one or more collection reservoirs. The selected enzyme is capable of catalyzing a reaction with the extracted analyte to the extent that a product of this reaction can be sensed, e.g., can be detected electrochemically from the generation of a current which current is detectable and proportional to the amount of the analyte which is reacted. In one embodiment of the present invention, a suitable enzyme is glucose oxidase, which oxidizes glucose to gluconic acid and hydrogen peroxide. The subsequent detection of hydrogen peroxide on an appropriate biosensor electrode generates two electrons per hydrogen peroxide molecule creating a current that can be detected and related to the amount of glucose entering the device. Glucose oxidase (GOx) is readily available commercially and has well known catalytic characteristics. However, other enzymes can also be used, as long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, urea with a urease system, cholesterol with a cholesterol oxidase system, and theophylline with a xanthine oxidase system.

In addition, the oxidase enzyme (used for hydrogen peroxidase-based detection) can be replaced with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea. Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytion), chemotherapy (e.g., adriamycin), hyperactivity (e.g., ritalin), and anti-organ-rejection (e.g., cyclosporin).

Preferably, the biosensor electrode must be able to detect the analyte which has been extracted into the one or more collection reservoirs when present at nominal concentration levels. Suitable biosensor electrodes and associated sampling systems as described in are described in PCT Publication Nos. WO 97/10499, published 20 Mar. 1997 and WO 98/42252, published 1 Oct. 1998.

In one embodiment of the ionically conductive medium of the present invention, the hydrogel comprises approximately the following proportions of components: 0.90 wt % sodium chloride, 0.22 wt % sodium phosphate monobasic, 2.25 wt % sodium phosphate dibasic, 0.20 wt % sodium undecylenate, 10.0 wt % Polyox™-brand polyethylene oxide (approximately 600,000 MW, available from Union Carbide, Danbury Conn.), 0.64 wt % glucose oxidase and 85.87 wt % purified water (note that the wt % of glucose oxidase can vary depending on the activity of the glucose oxidase typically 1,000 units of glucose oxidase is employed in this formulation—adjustment in water wt % can be used to "round-out" the total wt % of the formulation). In another embodiment of the ionically conductive medium of the present invention, the hydrogel comprises approximately the following proportions of components: 0.90 wt % NaCl, 0.32 wt % sodium phosphate monobasic, 2.07 wt % sodium phosphate dibasic, 0.20 wt % Nipastat ® biocide, 10.0 wt % Polyox™-brand polyethylene oxide (approximately 600,000 MW), 0.64 wt % glucose oxidase and 85.87 wt % purified water (note that the wt % of glucose oxidase can vary depending on the activity of the glucose oxidase typically 1,000 units of glucose oxidase is employed in this formulation—adjustment in water wt % can be used to "round-out" the total wt % of the formulation). In yet another embodiment of the ionically conductive medium of the present invention, the hydrogel comprises approximately the following proportions of components: 0.90 wt % NaCl, 0.26 wt % sodium phosphate monobasic, 2.17 wt % sodium phosphate dibasic—7 $H_2O$, 0.20 wt % Nipastat® biocide, 10.00 wt % Polyox™-brand polyethylene oxide (approximately 600,000 MW), 1.00 wt % bisacrylamide (2% solution), glucose oxidase to give 1000 units of enzymatic activity per gram of gel and the remaining volume in purified water.

The concentration of the biocide is typcially based on the concentration of the biocide wherein it acts effectively as a biocide. This concentration can vary depending on the selected biocide and suitable concentrations can be tested for efficacy as discussed herein. A typical range for the biocide concentration is about 0.01 wt % to 5 wt %, preferably between about 0.1 wt % to about 1 wt %, more preferably between about 0.2 wt % and 0.5 wt %.

4. Exemplary Sampling Systems

An automatic sampling system may be used to monitor levels of analyte, for example, glucose, in a biological system via the transdermally extraction of the analyte (e.g., glucose) from the biological system, particularly an animal subject. Transdermal extraction is carried out by applying an electrical current or ultrasonic radiation to a tissue surface at a collection site. The electrical current is used to extract small amounts of glucose from the subject into a collection reservoir. The collection reservoir is in contact with a sensor element (biosensor) which provides for measurement of glucose concentration in the subject. As glucose is transdermally extracted into the collection reservoir, the analyte reacts with the glucose oxidase within the reservoir to produce hydrogen peroxide. The presence of hydrogen peroxide generates a current at the biosensor electrode that is directly proportional to the amount of hydrogen peroxide in the reservoir. This current provides a signal which can be detected and interpreted (for example, employing an algorithm using statistical methods) by an associated system controller to provide a glucose concentration value or amount for display.

In the use of the sampling system, a collection reservoir is contacted with a tissue surface, for example, on the stratum corneum of a subject's skin. An electrical current is then applied to the tissue surface in order to extract glucose from the tissue into the collection reservoir. Extraction is carried out, for example, continually over a period of about 12 hours. The collection reservoir is analyzed, at least periodically, to measure glucose concentration therein. The measured value correlates with the subject's blood glucose level.

To sample the analyte, one or more collection reservoirs are placed in contact with a tissue surface on a subject. The ionically conductive material within the collection reservoir is also in contact with an electrode (for reverse iontophoretic extraction) which generates a current sufficient to extract glucose from the tissue into the collection reservoir. Referring to FIG. 1, an exploded view of exemplary components comprising one embodiment of an autosensor for use in an iontophoretic sampling system is presented. The autosensor components include two biosensor/iontophoretic electrode assemblies, 104 and 106, each of which have an annular iontophoretic electrode, respectively indicated at 108 and 110, which encircles a biosensor electrode 112 and 114. The electrode assemblies 104 and 106 are printed onto a polymeric substrate 116 which is maintained within a sensor tray 118. A collection reservoir assembly 120 is arranged over the electrode assemblies, wherein the collection reservoir assembly comprises two hydrogel inserts 122 and 124 retained by a gel retaining layer 126 and mask layer 128. Further release liners may be included in the assembly, for example, a patient liner 130, and a plow-fold liner 132. In an alternative embodiment, the electrode assemblies can include bimodal electrodes. A polyurethane mask layer 128 as described in PCT Publication No. WO 97/10356, published 20 Mar. 1997, may be present. Other embodiments of the autosensor are described in WO 99/58190, "Collection Assemblies for Transdermal Sampling System," T. E. Conn, et al.

The mask and retaining layers are preferably composed of materials that are substantially impermeable to the analyte (e.g., glucose) to be detected (see, for example, U.S. Pat. Nos. 5,735,273, and 5,827,183). By "substantially impermeable" is meant that the material reduces or eliminates analyte transport (e.g., by diffusion). The material can allow for a low level of analyte transport, with the proviso that the analyte that passes through the material does not cause significant edge effects at the sensing electrode used in conjunction with the mask and retaining layers. Examples of materials that can be used to form the layers include, but are not limited to polyester, polyester derivatives, other polyester-like materials, polyurethane, polyurethane derivatives and other polyurethane-like materials.

The components shown in exploded view in FIG. 1 are intended for use in a automatic sampling system which is configured to be worn like an ordinary wristwatch, as described in PCT Publication No. WO 96/00110, published 4 Jan. 1996. The wristwatch housing can further include suitable electronics (e.g., microprocessor, memory, display and other circuit components) and power sources for operating the automatic sampling system. The sensing electrode can be a Pt-comprising electrode configured to provide a geometric surface area of about 0.1 to 3 $cm^2$, preferably about 0.5 to 2 $cm^2$, and more preferably about 1 $cm^2$. This particular configuration is scaled in proportion to the collection area of the collection reservoir used in the sampling system of the present invention, throughout which the extracted analyte and/or its reaction products will be present. The electrode composition is formulated using analytical- or electronic-grade reagents and solvents which ensure that electrochemical and/or other residual contaminants are avoided in the final composition, significantly reducing the background noise inherent in the resultant electrode. In particular, the reagents and solvents used in the formulation of the electrode are selected so as to be substantially free of electrochemically active contaminants (e.g., anti-oxidants), and the solvents in particular are selected for high volatility in order to reduce washing and cure times.

The reactive surface of the sensing electrode can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (Analytical Chemistry 67(24), 4594–4599, 1995).

Any suitable iontophoretic electrode system can be employed, however it is preferred that a silver/silver chloride (Ag/AgCl) electrode system is used. The iontophoretic electrodes are formulated typically using two performance parameters: (1) the electrodes are capable of continual operation for extended periods, preferably periods of up to 24 hours or longer; and (2) the electrodes are formulated to have high electrochemical purity in order to operate within the present system which requires extremely low background noise levels. The electrodes must also be capable of passing a large amount of charge over the life of the electrodes. With regard to continual operation for extended periods of time, Ag/AgCl electrodes are capable of repeatedly forming a reversible couple which operates without unwanted electrochemical side reactions (which could give rise to changes in pH, and liberation of hydrogen and oxygen due to water hydrolysis). The Ag/AgCl electrode is thus formulated to withstand repeated cycles of current passage in the range of about 0.01 to 1.0 mA per $cm^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also formulated using analytical- or electronic-grade reagents and solvents, and the polymer binder composition is selected to be free of electrochemically active contaminants which could diffuse to the biosensor to produce a background current.

The automatic sampling system can transdermally extract the sample in a continual manner over the course of a 1–24 hour period, or longer, using reverse iontophoresis. The collection reservoir comprises an ionically conductive medium, preferably the hydrogel medium described hereinabove. A first iontophoresis electrode is contacted with the collection reservoir (which is typically in contact with a target, subject tissue surface), and a second iontophoresis electrode is contacted with either a second collection reservoir in contact with the tissue surface, or some other ionically conductive medium in contact with the tissue. A power source provides an electric potential between the two electrodes to perform reverse iontophoresis in a manner known in the art. As discussed above, the biosensor selected to detect the presence, and possibly the level, of the target analyte (for example, glucose) within a reservoir is also in contact with the reservoir.

In practice, an electric potential (either direct current or a more complex waveform) is applied between the two iontophoresis electrodes such that current flows from the first electrode through the first conductive medium into the skin, and back out from the skin through the second conductive medium to the second electrode. This current flow extracts substances through the skin into the one or more collection reservoirs through the process of reverse iontophoresis or electroosmosis. The electric potential may be applied as described in PCT Publication No. WO 96/00110, published 4 Jan. 1996.

As an example, to extract glucose, the applied electrical current density on the skin or tissue can be in the range of about 0.01 to about 2 $mA/cm^2$. In order to facilitate the extraction of glucose, electrical energy can be applied to the electrodes, and the polarity of the electrodes can be, for example, alternated so that each electrode is alternately a cathode or an anode. The polarity switching can be manual or automatic.

When a bimodal electrode is used, during the reverse iontophoretic phase, the power source provides a current flow to the first bimodal electrode to facilitate the extraction of the chemical signal into the reservoir. During the sensing phase, the power source is used to provide voltage to the first sensing electrode to drive the conversion of chemical signal retained in reservoir to electrical signal at the catalytic face of the sensing electrode. The power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode subassembly can be operated by electrically connecting the bimodal electrodes such that each electrode is capable of functioning as both an iontophoretic electrode and counter electrode along with appropriate sensing electrode(s) and reference electrode(s), to create standard potentiostat circuitry.

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present invention, the electrical current measured at the sensing electrode subassembly is the current that is correlated with an amount of chemical signal corresponding to the analyte.

The detected current can be correlated with the subject's blood glucose concentration (typically using statistical algorithms associated with a microprocessor) so that the system controller may display the subject's actual blood glucose concentration as measured by the sampling system. For example, the system can be calibrated to the subject's actual blood glucose concentration by sampling the subject's blood during a standard glucose tolerance test, and analyzing the blood glucose using both a standard blood glucose monitor and the sampling system of the present invention. In addition or alternately, the sampling system can be calibrated at a calibration time point where the signal obtained from the sampling system at that time point is correlated to blood glucose concentration at that time point as determined by direct blood testing (for example, glucose concentration can be determined using a HemoCue® clinical analyzer (HemoCue AB, Sweden)). In this manner, measurements obtained by the sampling system can be correlated to actual values using known statistical techniques. Such statistical techniques can be formulated as algorithm(s) and incorporated in a microprocessor associated with the sampling system.

Further, the sampling system can be pre-programmed to begin execution of its signal measurements (or other functions) at a designated time. One application of this feature is to have the sampling system in contact with a subject and to program the sampling system to begin sequence execution during the night so that it is available for calibration immediately upon waking. One advantage of this feature is that it removes any need to wait for the sampling system to warm-up before calibrating it.

5. Selectively Permeable Barriers

Further aspects of the present invention include, methods of generating a selectively permeable barrier on an electrode surface, as well as, further means for reducing the presence of a compound in an ionically conductive material. In one embodiment, the presence of the compound interferes with detecting an analyte in the material. Previously it has been required that the membrane film (i.e., selectively permeable barrier) be formed a priori on an electrode and this represents an additional step during the fabrication of a biosensor assembly. This represents a key disadvantage of the technique as it has been practiced heretofore. Experiments performed in support of the present invention demonstrate a one-step method for the formation of a permselective membrane to reduced interferences. For example, in the context of glucose detection, glucose entering the hydrogel is converted to $H_2O_2$, which diffuses through the membrane film with little or no attenuation, whereas larger interfering molecules, such as uric acid and acetaminophen, are significantly attenuated, resulting in an enhanced selectivity of the $H_2O_2$ (from enzymatic oxidation of glucose) response at the sensor surface.

Accordingly, in one aspect of the invention, interfering species are reduced by polymerizing an interfering compound to form an electrochemically-inactive but permeation selective barrier at the reactive face of the sensor means. The permeation selective characteristics of the polymer barrier can provide the added benefit of reducing signals generated from interferants other than the species being polymerized. Because the aforementioned permeation selective barrier is created on the reactive face of the sensor means in situ rather than prior to construction of the collection assembly, the present invention provides efficient means for manufacturing collection assemblies that use this method for reducing the presence of an interferant compound.

Examples 4, 5 and 6 describe the polymerization of compounds, e.g., biocides, and formation of a polymer barrier (polymer film) at the reactive face of a sensor electrode. The polymer barrier formed has been shown to selectively screen some interfering species (molecules), while at the same time allowing accurate quantitation of an analyte of interest. In addition to generating a selectively permeable barrier, polymerization of the compound also serves to reduce the concentration of the compound in the ionically conductive media.

In one aspect of the present invention, the the ionically conductive material, comprising the compound, is placed in contact with a reactive face of a sensor element such that, when an electric current is flowing to the sensor element, the current flows through the ionically conductive material. The sensor element is then activated to provide the electrical current for a period of time and under conditions sufficient to polymerize the compound on the reactive face of the sensor element, thus reducing the presence of the compound in the ionically conductive material. Such times and conditions can be determined for a variety of compounds, for example, methyl parabens, following the guidance of the specification and in particular the methods illustrated in Examples 4, 5 and 6.

The present invention also provides a method of forming a permeation selective barrier in situ on a reactive face of a sensor element. In this aspect of the invention, an ionically conductive material is formulated comprising a compound, for example, a phenolic compound, capable of polymerizing under the influence of an electrical current. The ionically conductive material is placed in contact with the reactive face of a sensor element such that when the electric current is flowing to the sensor element, the current flows through the ionically conductive material. The sensor element is activated to provide the electrical current for a period of time and under conditions sufficient to polymerize the compound on the reactive face of the sensor. Such polymerization serves to form a permeation selective barrier. In the case of a biocide, the polymerization also serves to reduce the concentration of the biocide in the ionically conductive material.

In a preferred embodiment of the present invention, the compound is a biocide, for example, a phenolic compound. Such a phenolic compound may, for example, be an ester of p-hydroxybenzoic acid, or mixture of such esters (e.g., methyl ester, ethyl ester, propyl ester, butyl ester, and isobutyl ester). Related biocides are discussed herein above.

Sensor elements useful in the practice of the present invention have also been described above. In a preferred embodiment the sensor element is a platinum/carbon electrode.

Numerous analytes are discussed herein, an exemplary analyte being glucose (see Examples 4, 5, and 6).

The present invention also includes collection assemblies for use in sampling systems. Typically, a collection insert layer comprises an ionically conductive material having a compound that will polymerize on a reactive face of a sensor element. The collection insert is placed in working, i.e., functional, relationship with the reactive face. Such a collection insert may be part of an autosensor assembly and may include a support tray as well (see, e.g., FIG. 1).

Also included in the present invention are methods of manufacturing such collection assemblies (or autosensor assemblies). Such methods include formulating the ionically conductive medium to contain the compound, wherein the ionically conductive material has a first surface and a second surface. The first surface of the ionically conductive medium is then placed in contact with a mask layer. Mask layers were discussed above and typically comprise a material that is substantially impermeable to the selected analyte or derivatives thereof. The mask layer (i) has an inner face and an outer face and the inner face is positioned in facing relationship with the first surface of the ionically conductive medium, and (ii) defines an opening that exposes at least a portion of the first surface of the ionically conductive medium. The second surface of the ionically conductive medium is contacted with a retaining layer. The retaining layer has an inner face and an outer face wherein the inner face is positioned in facing relationship with the second surface of the ionically conductive medium. The retaining layer defines an opening that exposes at least a portion of the second surface of the ionically conductive medium to form the collection assembly. The ionically conductive media may further comprise an enzyme composition and other components as discussed above. For example, the ionically conductive media may be hydrogels comprising an enzyme capable of reacting with an analyte to produce hydrogen peroxide, and a phenolic compound that will polymerize under an electric current. The method may further include placing a sensor element in operative contact with the ionically conductive media (e.g., collection insert layer). In one embodiment, upon application of electrical energy, the sensor element reacts electrochemically with the phenolic compound to provide a selectively permeable barrier at an interface between the sensor element and the collection insert layer. Other components (such as a support tray) may be added during the manufacturing method, such as, the components shown in FIG. 1 and discussed above.

The present invention also includes devices (e.g., collection assemblies, laminates, and/or autosensors) made by these methods.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein, both supra and infra, are hereby incorporated by reference.

Experimental

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

EXAMPLE 1

Stability of the Nipastat® Biocide in the Hydrogel

Nipastat®-containing hydrogels were formulated with the appropriate buffer salts under standard conditions, from which samples were taken for analysis. After exposure to controlled environmental conditions (temperature and humidity) for differing periods of time, the sample hydrogels were extracted in acetonitrile (ACN)/water and assayed for the presence of methyl, ethyl, propyl and butyl esters of p-hydroxybenzoic acid using a reverse phase octadecylsilane (ODS) HPLC column as follows. The hydrogels were cut using a ¾ inch punch to generate the sample disks to assay. Each disk was added to 5 mL of acetonitrile/water (30% ACN, v/v) and the Nipastat® biocide was extracted for 1 hour while shaking on an orbital shaker at 100 rpm. The extract was then filtered through a 0.2 µm membrane prior to HPLC separation and UV detection at 254 nm.

Reverse phase HPLC chromatography was performed using a Waters 3.9 mm×15 cm Nova-Pak C-18 column (Milford, Mass.) operating at a flow rate of between about 1.0 to 2.0 mL/min. at 35° C. The eluent was monitored by UV at 254 nm using a Shimadzu SPD-10AU UV-Visible spectrometer (Kyoto, Japan). Samples 10 µL in volume were injected into the column equilibrated in 30% ACN in water, and the following 20-minute gradient program was performed:

1. Initial time of injection: 30% ACN/70% water at a flow rate of 1 mL/min
2. Linear Gradient from 30% ACN to 80% ACN for 9.0 minutes (1 mL/min)
3. Linear Gradient from 80% ACN to 100% ACN for 0.5 minutes (1 mL/min)
4. 100% ACN for 4.5 minutes (1 mL/min)
5. Linear Gradient from 100% ACN to 30% ACN for 0.5 minutes at a flow rate of 2 mL/min
6. 30% ACN for 5.5 minutes at a flow rate of 1 mL/min The HPLC profiles of the extracts were compared with that of a standard solution of known concentration comprising the p-hydroxybenzoate derivatives. The peak intensities of the experimental samples are compared to those of the standards to determine relative amounts of each extracted paraben. Typical retention times for the different esters of p-hydroxybenzoic acid were determined to be: 2.4 to 2.9 minutes for p-hydroxybenzoic acid methyl ester (methylparaben), 4.0 to 4.8 minutes for p-hydroxybenzoic acid ethyl ester (ethylparaben), 6.0 to 7.0 minutes for p-hydroxybenzoic acid propyl ester (propylparaben), and 7.5 to 8.5 minutes for the p-hydroxybenzoic acid butyl esters (butylparaben and isobutylparaben). The data (Table 1, presented ) indicate that the Nipastat® biocide is stable within the hydrogel, so any short term loss of compound is not due to degradation.

TABLE 1

Stability of Nipastat ® Biocide within Gel Laminate

| Time Point | Temperature | Relative Humidity | Biocide Content (%) | Percent of Theoretical Concentration (%) |
| --- | --- | --- | --- | --- |
| 0 | 40° C. | 75% | 0.15 | 75 |
| 2 weeks | 40° C. | 75% | 0.14 | 70 |
| 1 month | 40° C. | 75% | 0.13 | 65 |
| 3 months | 40° C. | 75% | 0.11 | 55 |
| 6 months | 40° C. | 75% | 0.11 | 55 |
| 0 | 25° C. | 60% | 0.15 | 75 |
| 1 month | 25° C. | 60% | 0.14 | 70 |
| 3 months | 25° C. | 60% | 0.13 | 65 |
| 6 months | 25° C. | 60% | 0.11 | 57 |

EXAMPLE 2

Migration of the Nipastat® Biocide into Components of the Biosensor Collection Assembly Collection assemblies incorporating Nipastat® biocide-comprising hydrogels were assayed for retention of the biocide within the hydrogel. Samples of the hydrogel prior to and after incorporation into the collection assembly, as well as the components of the collection assembly in contact with the hydrogel, were prepared as described in Example 1. The decreasing quantities of parabens extracted from the hydrogel indicate that, over time, the Nipastat® biocide migrates out of the hydrogel and into the adjacent collection assembly components. When the components of the collection assembly in contact with the hydrogel (liners, gel retaining layer, and mask) were assayed, it was determined that the Nipastat® biocide was migrating preferentially into the gel retaining layer (comprising a polyester derivative) and the mask layer (comprising a polyurethane derivative).

These results are presented in Tables 2 and 3, respectively. The liners (one comprising a polyethylene derivative and the other comprising a polypropylene derivative) showed negligible adsorption of the Nipastat® paraben components.

TABLE 2

Adsorption of Nipastat ® Paraben Components by Mask Layer Component of Collection Assembly after 48 Hours at 4° C.

|  | Methyl | Ethyl | Propyl | Butyl |
|---|---|---|---|---|
| Gel Control |  |  |  |  |
| 1 | 282756 | 93771 | 27621 | 75858 |
| 2 | 265561 | 58684 | 25936 | 68194 |
| 3 | 303549 | 69162 | 28226 | 79360 |
| 4 | 199735 | 43754 | 18744 | 50220 |
| 5 | 233495 | 52495 | 22146 | 59177 |
| Average | 257019 | 63573 | 24535 | 66562 |
| Std. Dev. | 41034 | 19252 | 4011 | 11984 |
| Gel + Mask |  |  |  |  |
| 1 | 5445 | 0 | 0 | 0 |
| 2 | 11776 | 285 | 0 | 0 |
| 3 | 13807 | 0 | 252 | 0 |
| 4 | 11268 | 0 | 0 | 436 |
| 5 | 8081 | 0 | 0 | 0 |
| Average | 10075 | 57 | 50 | 87 |
| Std. Dev. | 3304 | 127 | 113 | 195 |
| % Loss of Nipastat ® biocide from Gel | 96.1 | 99.9 | 99.8 | 99.9 |

TABLE 3

Adsorption of Nipastat ® Paraben Components by Gel Retaining Layer (GRL) Component of Collection Assembly after 9 Days at 4° C.

|  | Methyl | Ethyl | Propyl | Butyl |
|---|---|---|---|---|
| Gel Control |  |  |  |  |
| 1 | 313086 | 70588 | 30407 | 82288 |
| 2 | 256304 | 56529 | 24349 | 67760 |
| 3 | 250006 | 56747 | 22180 | 61920 |
| 4 | 261836 | 58534 | 24034 | 66552 |
| 5 | 315315 | 68190 | 30121 | 82337 |
| Average | 279309 | 62118 | 26218 | 72171 |
| Std. Dev. | 32135 | 6737 | 3786 | 9511 |
| Gel + GRL |  |  |  |  |
| 1 | 147682 | 23429 | 4958 | 1377 |
| 2 | 239356 | 43116 | 11465 | 15432 |
| 3 | 231307 | 38410 | 9664 | 8640 |
| 4 | 251620 | 46214 | 12662 | 17787 |
| 5 | 289836 | 53073 | 15618 | 20353 |
| Average | 231960 | 40848 | 10873 | 12718 |
| Std. Dev. | 52187 | 11099 | 3953 | 7691 |
| % Loss of Nipastat ® biocide from Gel | 17.0 | 34.2 | 58.5 | 82.4 |

EXAMPLE 3

Migration of the Biocide Sodium Undecylenate into Components of the Biosensor Collection Assembly Collection assemblies incorporating sodium undecylenate-comprising hydrogels were assayed for retention of the biocide within the hydrogel. The presence of undecylenic acid in the hydrogel and assembly components was determined by gas chromatography (GC) using a Hewlett Packard (Avondale, Pa.) 5890 gas chromatogram equipped with an HP 3396A integrator. The hydrogels and collection assembly components were cut using a ¾ inch punch to generate the samples to assay. Each sample "disk" was added to 4 mL of 1M HCl, and the undecylenic acid was extracted for 2 hours while shaking on an orbital shaker at 150 rpm, followed by 10 minutes at 100 rpm. The sample disks were then extracted twice with 4 mL of ethyl acetate. Samples 1 µL in volume were injected into the GC and the results compared to that generated for a standard solution of undecylenic acid.

The undecylenic acid was also shown to migrate out of the hydrogel and into the adjacent collection assembly components over time, as indicated by decreasing quantities of biocide extracted from the hydrogel two weeks after incorporation into the collection assembly (Table 2.) Hydrogels comprising undecylenic acid exposed solely to the polyurethane mask component, or the polyester gel retaining layer also demonstrated loss of undecylenic acid from the hydrogel over time.

TABLE 4

Adsorption of Undecylenic Acid into Mask Layer and Gel Retaining Layer (GRL) Components of Collection Assembly after Two Weeks at Room Temperature

| Hydrogel Sample | % Loss for Gel Control | % Loss for Gel + Mask Layer | % Loss for Gel + GRL |
|---|---|---|---|
| 1 | 37.2 | 78.2 | 22.2 |
| 2 | 52.8 | 72.5 | 24.7 |
| 3 | 64.9 | 73.3 | 37.0 |
| 4 | 68.1 | 68.5 | 28.4 |
| 5 | 75.2 |  |  |
| 6 | 76.2 |  |  |
| Average | 62.4 | 73.1 | 28.1 |
| Std. Dev. | 15.0 | 4.0 | 6.5 |

EXAMPLE 4

Electropolymerization of 0.2% Nipastat® Biocide Directly onto Pt/C Electrodes

The polymerization of the Nipastat® biocide and formation of a polymer barrier (polymer film) at the reactive face of the Pt/C sensor electrode was demonstrated as follows. Experiments were performed using a BAS 100W/B potentiostat (Bioanalytical Systems, West Lafayette Ind.). The electropolymerization reactions were initiated by either (a) cycling the electrode immersed in 0.2% Nipastat® biocide solution between −0.2 and 1.0V vs. Ag/AgCl, or (b) by applying a constant potential (0.77V vs. AgCl) for 10 to 40 minute intervals. The modified electrodes were immersed in phosphate buffer (pH 7.4) overnight to remove loosely bound material. The samples were removed from the buffer solutions, rinsed gently with distilled water, and allowed to dry prior to use.

The following functional test was used to determine the sensitivity of the sensors element exposed to a Nipastat® biocide-containing solution, as compared to control sensing elements upon addition of glucose. The sensing element with the Nipastat®-derived polymer film was combined with the collection assembly comprising the ionically conductive material to form the autosensor assembly. The autosensor assembly was then preconditioned for 10 minutes at 0.77V, followed by 50 minutes at 0.42V. A glucose solution (200 µM) was deposited onto the ionically conductive material; this is preferably achieved by placing a circular absorbent disk, or "wick," against the ionically conductive medium to spread the glucose solution evenly across the surface of the material. The response of the sensor element is measured from this time forward.

Irreversible deposition of the Nipastat® biocide onto the sensing element was confirmed independently by comparing the response of the sensing element to 1 mM ferricyanide before and after electropolymerization of the biocide. The potential required for polymerization of the Nipastat® biocide onto the reactive face of the sensing element was determined to be between about 0.25V and about 1.0V, preferably between about 0.6V and about 0.9 V, most preferably at about 0.9V. Approximately 90% of the reactive face of the sensor element was blocked by polymerized biocide upon exposure of the sensor element to 0.77V for 10 minutes.

EXAMPLE 5

In Situ Polymerization of the Nipastat® Biocide onto the Sensing Electrode

Figure 2:
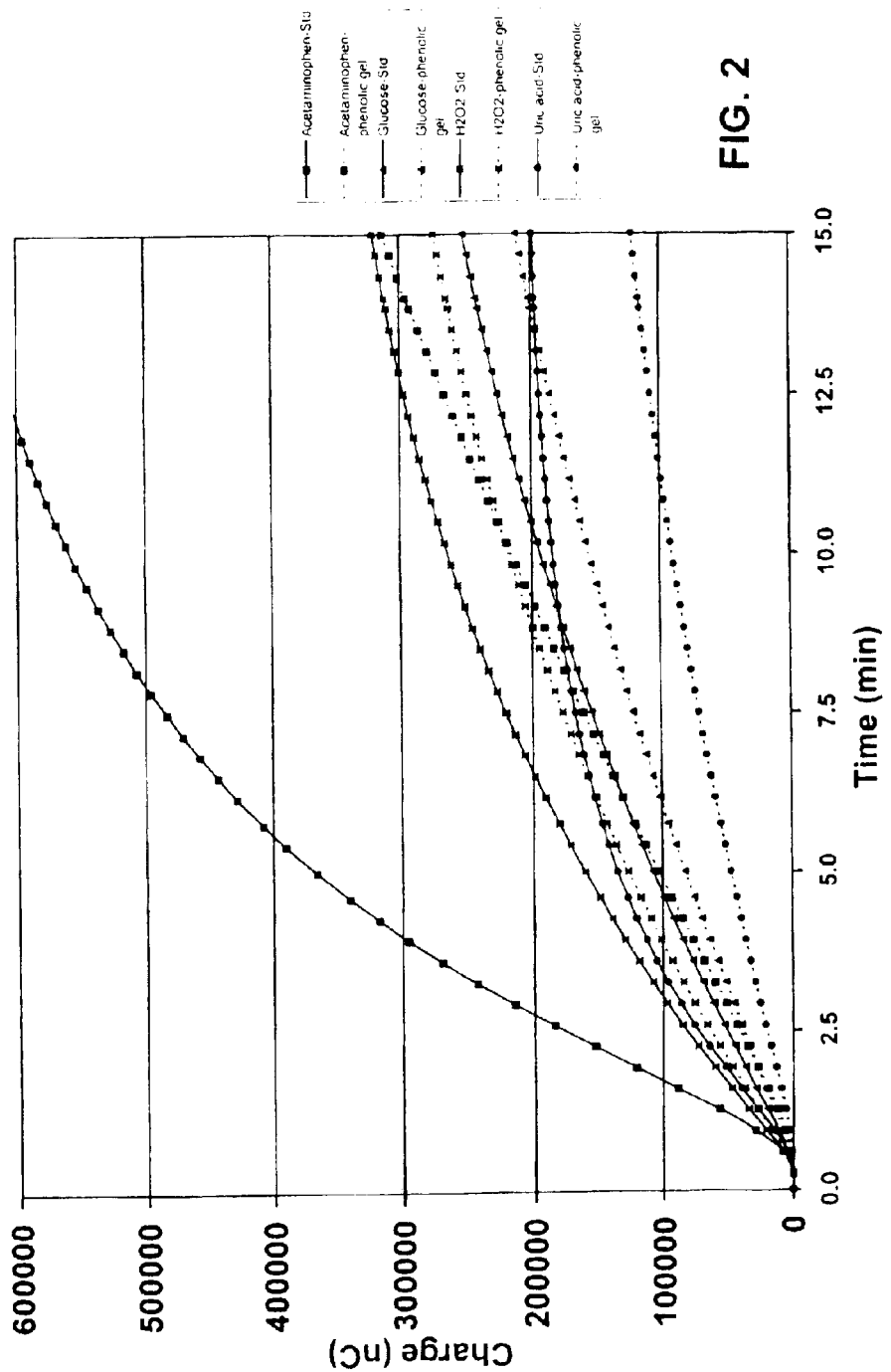
FIG. 2 depicts the response of sensor electrodes to various analytes in hydrogels in the presence or absence of phenolic compounds. Charge (y-axis) is depicted at various time intervals (x-axis). The solid squares with solid connecting lines depict the sensor electrodes' response to acetaminophen for a system containing a standard gel (i.e., without biocide); solid squares with dashed connecting lines represents the electrodes' response to acetaminophen in the presence of a phenolic gel; solid triangles with solid connecting lines represent the electrodes' response to glucose for a standard gel; solid triangles with dashed connecting lines represent the electrodes' response to glucose in the presence of a phenolic gel; solid double-triangles with solid connecting lines represent the electrodes' response to $H_2O_2$ in a standard gel; solid double-triangles with dashed connecting lines represent the electrodes' response to $H_2O_2$ in a phenolic gel; solid circles with solid connecting lines represent the electrodes' response to uric acid in a standard gel; and solid circles with dashed connecting lines represent the electrodes' response to uric acid in a phenolic gel.

The effectiveness of in situ formation of a phenolic compound-derived electropolymerized barrier (polymer film) at the reactive face of the Pt/C sensor electrode was demonstrated by measuring the response of the underlying Pt/C sensor electrode after deposition of known concentrations of model compounds on the hydrogels prepared in the presence and absence of the Nipastat® paraben compounds (FIG. 2). The list of model compounds tested included glucose (200 $\mu$M), hydrogen peroxide (200 $\mu$M), uric acid (100 $\mu$M), and acetaminophen (230 and 331 $\mu$M). The response of the sensor elements was measured upon exposure of the electrode to 200 $\mu$M glucose in the presence or absence of the model compound, in a manner similar to that used in Example 4. The sensing elements were combined with the collection assembly comprising the ionically conductive material containing the biocide, to form the autosensor assembly. The autosensor assembly was then preconditioned for 10 minutes at 0.77V, followed by 50 minutes at 0.42V, during which the polymerization of the biocide occurs. The glucose solution (200$\mu$M) plus the compounds to be analyzed were deposited onto the ionically conductive material, and the response of the sensor element measured from this time forward.

Table 5 demonstrates the time-dependent responses of the collection assemblies to the test compounds. The in situ membrane film formed by polymerization of the Nipastat® biocide at the reactive face of the sensor electrode attenuated the response of the collection assembly to the uric acid and acetaminophen. However, in situ formation of the membrane film had little impact on the response generated by addition of hydrogen peroxide or glucose. Thus, the in situ membrane film demonstrated selectivity with respect to the permeation properties (a "permselective" barrier).

Table 6 illustrates a similar observation at three discrete time points (2.5, 5.0 and 7.0 minutes, respectively) after application of the polarizing potential (i.e. after 60 minutes of "preconditioning"). The selectivity of the collection assembly into which hydrogels comprising Nipastat® biocide were incorporated indicates that the glucose and hydrogen peroxide responses are being retained while the uric acid and acetaminophen responses are reduced.

TABLE 6

Selectivity for Glucose against Interferants using Pt/C-sensing Electrode-Hydrogel System

| Compound | Hydrogel Composition | Selectivity Ratio | | |
|---|---|---|---|---|
| | | After 2.5 min | After 5.0 min | After 7.0 min |
| Uric acid | Standard | 1.43 | 1.26 | 1.11 |
| Uric acid | Nipastat ®-containing | 0.52 | 0.57 | 0.58 |
| Acetaminophen | Standard | 3.49 | 3.41 | 3.18 |
| Acetaminophen | Nipastat ®-containing | 1.08 | 1.25 | 1.31 |

The selectivity of the collection assembly can be expressed by the use of a selectivity ratio. The ratio is defines as the response (i.e. charge) generated by the interfering species divided by the response (charge) generated by the analyte, which in this embodiment is glucose.

$$\text{Selectivity Ratio} = \frac{\text{Response (charge) of interferant}}{\text{Response (charge) of analyte (glucose)}}$$

The smaller the selectivity ratio, the more selective a collection assembly is for the analyte. This ratio will be decreased (indicating a more selective analyte measurement) for high sensor responses to analyte (glucose) or for low responses to the interferant. Selectivity ratios for the interferants uric acid and acetaminophen are shown in Table 6. Comparison of the selectivity ratios shows improvement in the selectivity when Nipastat® biocide-comprising hydrogels are used in the collection assemblies for the detection of glucose. These data demonstrate that, in fluids containing electroactive interferants, the in situ formation of a membrane film provides an effective method for selective measurement of analytes such as, but not limited to, glucose.

TABLE 5

Responses of Pt/C-Sensing Electrode to Model Compounds

| Compound | Hydrogel Composition | Charge (nC) | | |
|---|---|---|---|---|
| | | After 2.5 min | After 5.0 min | After 7.0 min |
| $H_2O_2$ | Standard | 81766 ± 10019 | 160916 ± 17594 | 209663 ± 20396 |
| $H_2O_2$ | Nipastat ® - containing | 63398 ± −7849 | 126747 ± 13723 | 168126 ± 16407 |
| Glucose | Standard | 50814 ± 3768 | 107464 ± 6035 | 146066 ± 7149 |
| Glucose | Nipastat ® - containing | 37598 ± 2190 | 82402 ± 4006 | 114781 ± 4902 |
| Uric acid | Standard | 72630 ± 5491 | 135108 ± 6605 | 162773 ± 5640 |
| Uric acid | Nipastat ® - containing | 19558 ± 4007 | 47146 ± 9357 | 66494 ± 12520 |
| Acetaminophen | Standard | 177161 ± 29100 | 366212 ± 45477 | 464431 ± 45109 |
| Acetaminophen | Nipastat ® - | 40752 ± 15503 | 102906 ± 38278 | 150029 ± 54509 |

Additional factors which were evaluated for their effect of the efficacy of interferant response suppression included the sensitivity of the sensor electrode, the presence of surfactants and the duration of the preconditioning time at 0.77V. Interferant signal response was more attenuated with increasing sensitivity of the sensor electrode. Addition of a surfactant to either the hydrogel composition or to the reactive surface of the sensor element also led to attenuated interferant signal response. The attenuation in signal was determined to not be due to degradation of the glucose oxidase enzyme for the hydrogels comprising both surfactant and Nipastat® biocide.

The collection assemblies were preconditioned for different lengths of time before glucose or acetaminophen were deposited on the hydrogel. The response in the presence of acetaminophen decreased significantly with the length of the preconditioning time while the values for glucose remained constant. These results indicate that preconditioning times from zero minutes to about 1 hour, and more particularly from about 5 minutes to about 30 minutes led to in situ polymerization of the Nipastat® biocide and suppression of interferant signal without any loss in glucose response. The result is consistent with polymerization and deposition of the Nipastat®-based film as a function of time.

EXAMPLE 6

Response of the Sensing Electrode to Glucose, Acetaminophen and Uric Acid in the Presence of Nipastat® Biocide Versus Undecylenic Acid Two biocides were compared with respect to the effects their presence (within the ionically conductive medium) had on signal generation at the sensing element under three conditions: in the presence of glucose, glucose plus acetaminophen, and glucose plus uric acid. The Nipastat® biocide was shown in the examples above to form a permeation selective barrier at the reactive face of the sensor element. The second biocide tested, undecylenic acid, was not expected to polymerize under the iontophoretic conditions used during the functionality test as described in the previous example. The measured responses of the sensor elements are presented in Table 7, normalized to a control "background" response for each sensor element. As described in Example 5, the sensor electrodes were assembled with the collection insert layer containing the appropriate ionically conductive material (control, Nipastat® biocide, or undecylenic acid biocide) to form the autosensor assemblies. The autosensor assemblies were preconditioned for 10 minutes at 0.77V, followed by 50 minutes at 0.42V, after which the glucose solution (200 $\mu$M) plus or minus the interferant species was deposited onto the ionically conductive material, and the response of the sensor element measured from this time forward. The results confirm that Nipastat® biocide forms a permeation selective barrier which selectively impedes acetaminophen and uric acid signal generation, while the undecylenic acid does not. The higher background measurements seen in the presence of Nipastat® biocide and undecylenic acid, indicating that these compounds are electrochemically active, and thus could potentially act as interferants themselves.

TABLE 7

Response of the Sensing Electrode to Glucose, Acetaminophen and Uric Acid in the Presence of Nipastat ® Biocide versus Sodium Undecylenate

| | | Percent Recovery in the Presence of 200 $\mu$M Glucose | | |
| --- | --- | --- | --- | --- |
| Sample | Replicate | Control Gel (% Recovery)* | Gel + Nipastat ® (% Recovery)* | Gel + Na-Undecylate (% Recovery)* |
| Glucose alone | 1 | 40.8 | 25.0 | 38.9 |
| Glucose alone | 2 | 39.3 | 28.9 | 49.2 |
| Glucose alone | 3 | 31.3 | 46.8 | 48.7 |
| Glucose alone | 4 | 40.2 | 36.1 | 52.7 |
| Glucose alone | 5 | 38.2 | 27.3 | 53.9 |
| Glucose alone | 6 | 39.9 | 28.4 | 53.1 |
| Average | | 38.3 | 32.1 | 49.4 |
| Standard Deviation | | 3.5 | 8.1 | 5.6 |
| Background (nA) | | 33.8 | 59.5 | 79.8 |
| 331 uM acetaminophen | 1 | 137.9 | 77.7 | 143.8 |
| 331 uM acetaminophen | 2 | 138.6 | 98.2 | 155.6 |
| 331 uM acetaminophen | 3 | 136.4 | 46.3 | 106.9 |
| 331 uM acetaminophen | 4 | 145.8 | 78.2 | 86.5 |
| 331 uM acetaminophen | 5 | 123.3 | 53.9 | 114.3 |
| 331 uM acetaminophen | 6 | 127.4 | 60.9 | 153.0 |
| Average | | 134.9 | 69.2 | 126.7 |
| Standard Deviation | | 8.2 | 19.1 | 28.2 |
| Background (nA) | | 27.7 | 55.7 | 75.8 |
| 100 uM uric acid | 1 | 77.4 | 48.8 | 72.4 |
| 100 uM uric acid | 2 | 73.2 | 43.5 | 62.6 |

TABLE 7-continued

Response of the Sensing Electrode to Glucose, Acetominophen and Uric Acid in the Presence of Nipastat ® Biocide versus Sodium Undecylenate

| Sample | Replicate | Control Gel (% Recovery)* | Gel + Nipastat ® (% Recovery)* | Gel + Na-Undecylate (% Recovery)* |
|---|---|---|---|---|
| | | Percent Recovery in the Presence of 200 µM Glucose | | |
| 100 uM uric acid | 3 | 68.3 | 60.7 | 75.7 |
| 100 uM uric acid | 4 | 71.9 | 31.8 | 80.0 |
| 100 uM uric acid | 5 | 56.8 | 55.9 | — |
| 100 uM uric acid | 6 | 72.5 | 54.7 | — |
| Average | | 70.0 | 49.3 | 72.7 |
| Standard Deviation | | 7.1 | 10.4 | 7.4 |
| Background (nA) | | 32.3 | 62.5 | 111.8 |

*Percent Recoveries (% recovery) were computed at five minutes after deposition of sample.

EXAMPLE 7

Microbial Challenge of Tonically Conductive Media in the Presence of Nipastat® Biocide Versus Undecylenic Acid Nipastat® biocide and undecylenic acid were compared with respect to the effects their presence (within the ionically conductive medium) had on microbial growth over time. A modified USP antimicrobial preservative effectiveness test was performed, using *Aspergillus niger*, *Candida albicans*, *Eschericia coli*, *Pseudomonas aeruginosa* and *Staphylococcus aureus*. Separate portions of the two hydrogels were inoculated with a low concentration of one of the listed microorganisms, and recovery of the microorganism was determined over a period of 28 days. For this assay, the microorganisms were cultured, harvested and diluted to yield working suspensions of $2.0 \times 10^3$ to $2.0 \times 10^4$ colony forming units (CFUs)/sample. Both the Nipastat® biocide and the undecylenic acid retained their biocide activity within the hydrogel, and were shown to be effective at reducing the microbial count across the 28 day period tested. The undecylenic acid was more effective than the Nipastat® biocide against the *Aspergillus niger*, *Pseudomonas aeruginosa* and *Staphylococcus aureus* inoculations. Both biocides were equally effective versus the *Candida albicans* and *Eschericia coli* inoculations.

What is claimed is:

1. A collection assembly for use in a glucose sampling system and for electrochemical detection of an amount or concentration of glucose, said collection assembly comprising:
   a collection insert layer comprising a first hydrogel having a first surface and a second surface, said first hydrogel comprising:
      polyethylene oxide present in an amount of about 5% to about 20% by weight based on the total weight of the hydrogel;
      water in an amount of about 50% or more and about 95% or less based on the total weight of the hydrogel;
      a chloride salt, wherein background electrical signal in the gel is less than approximately 200 nA;
      a phosphate buffer in an amount sufficient to maintain a pH in the hydrogel in the range of 6 to 8;
      an enzyme composition comprising glucose oxidase, said glucose oxidase present in an amount of from about 10 units to about 5,000 units per gram of the total weight of the hydrogel; and
      a biocide comprising an undecylenate;
   a mask layer comprising a material that is substantially impermeable to glucose and derivatives thereof, wherein the mask layer (i) has an inner face and an outer face and the inner face is positioned in facing relationship with the first surface of the first hydrogel and (ii) defines a first opening that exposes at least a portion of the first surface of the first hydrogel; and
   a gel retaining layer comprising an inner face and an outer face wherein (i) the inner face is positioned in facing relationship with the second surface of the first hydrogel, and (ii) the gel retaining layer defines a first opening that exposes at least a portion of the second surface of the first hydrogel.

2. The collection assembly of claim 1, wherein said collection assembly is a laminate.

3. The collection assembly of claim 1, further comprising a liner in contact with the mask layer.

4. The collection assembly of claim 3, further comprising a plow-fold liner in contact with the gel retaining layer.

5. The collection assembly of claim 1, wherein structural integrity of the hydrogel includes crosslinking the polyethylene oxide.

6. The collection assembly of claim 5, wherein said crosslinking is achieved by thermal reaction, chemical reaction, or providing ionizing radiation.

7. The collection assembly of claim 6, wherein said ionizing radiation is provided by electron beam radiation, UV radiation, or gamma radiation.

8. The collection assembly of claim 1, wherein said biocide comprises undecylenic acid, a salt of undecylenic acid, or mixtures thereof.

9. The collection assembly of claim 1, wherein said background electrical signal is less than approximately 50 nA.

10. The collection assembly of claim 1, wherein said enzyme composition further comprises a mutarotase enzyme.

11. The collection assembly of claim 1, wherein (i) said glucose oxidase can catalyze a reaction between glucose and oxygen resulting in the generation of hydrogen peroxide, and (ii) hydrogen peroxide degradative components of the enzyme composition are reduced such that quantitation of hydrogen peroxide produced by the glucose oxidase reaction is not compromised.

12. The collection assembly of claim 1, wherein said hydrogel further comprises a structural support material embedded in the hydrogel.

13. The collection assembly of claim 1, wherein one or more components of said hydrogel have been treated to remove compounds that cause background electrical signal.

14. The collection assembly of claim 13, wherein one or more of said hydrogel components have been treated using a diafiltration procedure to remove electroactive compounds therefrom.

15. The collection assembly of claim 1, wherein said hydrogel further comprises bisacrylamide.

16. The collection assembly of claim 1, wherein said biocide is present in the hydrogel at a concentration of between about 0.01% to about 5% based on the total weight of the hydrogel.

17. The collection assembly of claim 16, wherein said biocide is present in the hydrogel at a concentration of between about 0.1% to about 1% based on the total weight of the hydrogel.

18. The collection assembly of claim 17, wherein said biocide is present in the hydrogel at a concentration of between about 0.2% to about 0.5% based on the total weight of the hydrogel.

19. The colleetion assembly of claim 1, wherein the collection insert layer further comprises a second hydrogel having a first surface and a second surface, said second hydrogel comprising:

polyethylene oxide present in an amount of about 5% to about 20% by weight based on the total weight of the hydrogel;

water in an amount of about 50% or more and about 95% or less based on the total weight of the hydrogel;

a chloride salt, wherein background electrical signal in the gel is less than approximately 200 nA;

a phosphate buffer in an amount sufficient to maintain a pH in the hydrogel in the range of 6 to 8;

an enzyme composition comprising glucose oxidase, said glucose oxidase present in an amount of from about 10 units to about 5,000 units per gram of the total weight of the hydrogel; and a biocide comprising an undecylenate;

said inner face of the mask layer (i) is positioned in facing relationship with the first surface of the second hydrogel, and (ii) defines a second opening that exposes at least a portion of the first surface of the second hydrogel;

said inner face of the gel retaining layer (i) is positioned in facing relationship with the second surface of the second hydrogel, and (ii) defines a second opening that exposes at least a portion of the second surface of the second hydrogel.

* * * * *